United States Patent
Chen et al.

(10) Patent No.: US 8,272,738 B2
(45) Date of Patent: Sep. 25, 2012

(54) APPARATUS AND METHOD FOR RECOGNIZING A PERSON'S GAZE

(75) Inventors: Wen-Yih Chen, Jhongli (TW); Jang-Zern Tsai, Jhongli (TW)

(73) Assignee: National Central University, Jhongli, Taoyuan County (TW)

( * ) Notice: Subject to any disclaimer, the term of this patent is extended or adjusted under 35 U.S.C. 154(b) by 527 days.

(21) Appl. No.: 12/563,250

(22) Filed: Sep. 21, 2009

(65) Prior Publication Data

US 2010/0220290 A1    Sep. 2, 2010

(30) Foreign Application Priority Data

Mar. 2, 2009    (TW) ................................ 98106727 A

(51) Int. Cl.
*A61B 3/14* (2006.01)
(52) U.S. Cl. ........................................ 351/210; 351/246

(58) Field of Classification Search .................. 351/210, 351/209, 246, 205, 200
See application file for complete search history.

(56) References Cited

U.S. PATENT DOCUMENTS 7,862,172 B2 *   1/2011   Yoshinaga et al. ............ 351/210

* cited by examiner

*Primary Examiner* — Hung Dang
(74) *Attorney, Agent, or Firm* — Thomas, Kayden, Horstemeyer & Risley, LLP

(57) ABSTRACT

An apparatus and a method for recognizing a person's gaze are disclosed, where the apparatus includes a main body, an eye-movement detector, a data generator and a transmitter, where the main body has the specific area. The eye-movement detector can detect whether a gaze is fixed on the specific area. The data generator can generate gaze data when the gaze is fixed on the specific area. The transmitter can transmit the gaze data to terminal equipment, so that the terminal equipment can receive information that the gaze is fixed on the specific area based on the gaze data, so that the terminal equipment can provide a prompt based on the gaze data.

11 Claims, 7 Drawing Sheets

APPARATUS AND METHOD FOR RECOGNIZING A PERSON'S GAZE

RELATED APPLICATIONS

This application claims priority to Taiwan Application Serial Number 98106727, filed Mar. 2, 2009, which is herein incorporated by reference.

BACKGROUND

1. Technical Field

The present disclosure relates to an electronic device. More particularly, the present disclosure relates to an apparatus and a method for recognizing a person's gaze.

2. Description of Related Art

There is a trend nowadays for communications technology to be increasingly development. This in conjunction with the fact that such technology offers not only enhanced mobility but also true convenience for the user.

People communicate with each other through communication products; however, emotional communication seems so weak. Particularly in the case of telephone or electronic mail, it is difficult to transmit a subtle emotion showing in a user's eyes to the other party.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

According to one embodiment of the present invention, an apparatus for recognizing a person's gaze comprises a main body, an eye-movement detector, a data generator and a transmitter, where the main body has the specific area. The eye-movement detector can detect whether a gaze is fixed on the specific area. The data generator can generate first gaze data when the gaze is fixed on the specific area. The transmitter can transmit the first gaze data to terminal equipment, so that the terminal equipment can receive information that the gaze is fixed on the specific area based on the first gaze data, so that the terminal equipment can provide a prompt based on the first gaze data.

According to another embodiment of the present invention, a method for recognizing a person's gaze comprises steps as follows. First, a gaze is detected. The method then determines whether the gaze is fixed on a specific area or not. Next, first gaze data is generated when the gaze is fixed on the specific area. Then, the first gaze data is transmitted to terminal equipment, so that the terminal equipment can provide a prompt based on the first gaze data.

Many of the attendant features will be more readily appreciated as the same becomes better understood by reference to the following detailed description considered in connection with the accompanying drawings.

BRIEF DESCRIPTION OF THE DRAWINGS

The present description will be better understood from the following detailed description read in light of the accompanying drawings, wherein.

Like reference numerals are used to designate like parts in the accompanying drawings.

DESCRIPTION OF THE PREFERRED EMBODIMENTS

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

It will be understood that, although the terms first, second, etc. may be used herein to describe various elements, these elements should not be limited by these terms. These terms are only used to distinguish one element from another.

As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof. As used herein, the term "and/or" includes any and all combinations of one or more of the associated listed items.

Figure 1:
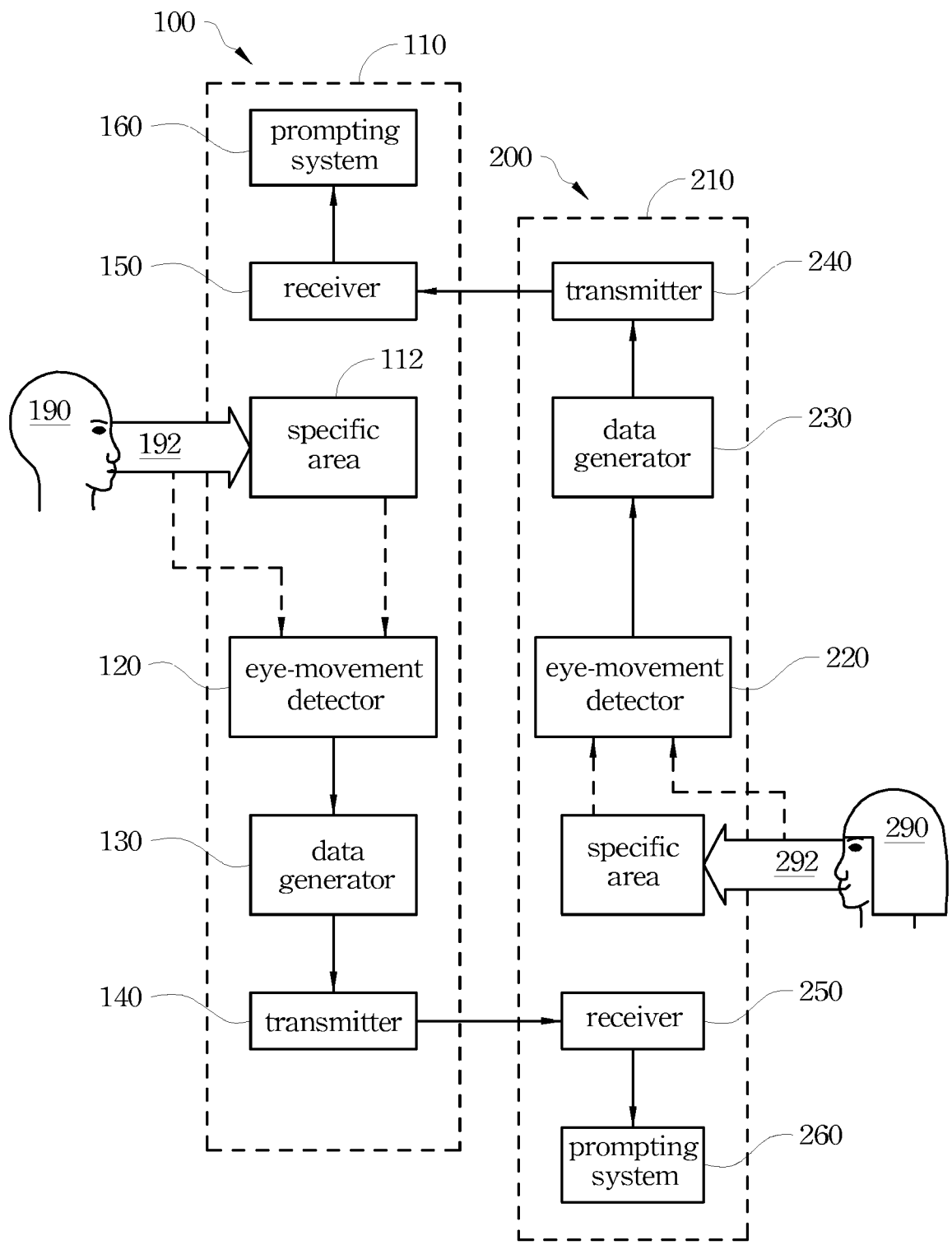
FIG. 1 is a block diagram illustrating an apparatus for recognizing a person's gaze according to one embodiment of the present invention.

Please refer to FIG. 1. FIG. 1 is a block diagram illustrating an apparatus 100 for recognizing a person's gaze according to one embodiment of the present invention. In FIG. 1, the apparatus 100 comprises a main body 110, an eye-movement detector 120, a data generator 130 and a transmitter 140, where the main body 110 includes the specific area 112 at which the subject is staring at.

The eye-movement detector 120 can detect whether a gaze 192 is fixed on the specific area 112; for example, the eye-movement detector 120 can detect a gaze 192 of a user 190 and then determine whether the gaze 192 is fixed on the specific area 112. The data generator 130 can generate first gaze data when the gaze 192 is fixed on the specific area 112. The transmitter 140 can transmit the first gaze data to terminal equipment 200, so that the terminal equipment 200 can receive information that the gaze is fixed on the specific area 112 based on the first gaze data.

In FIG. 1, the terminal equipment 200 comprises a receiver 250 and a prompting system 260. The receiver 250 can receive the first gaze data after the apparatus 100 sends the first gaze data. The prompting system 260 can provide a prompt based on the first gaze data; for example, the prompting system 260 may render prompting information, play prompting sound, vibrate itself or do the like. Thus, the user 290 knows that the gaze is fixed on the specific area 112 of the apparatus 100.

In practice, the terminal equipment 200 may be different form the apparatus 100; alternatively, the terminal equipment 200 is equal or similar to the apparatus 100, as shown in FIG. 1. In FIG. 1, the terminal equipment 200 comprises a main body 210, an eye-movement detector 220, a data generator 230 and a transmitter 240, where the main body 210 has the specific area 212.

The eye-movement detector 220 can detect whether a gaze 292 of the user 290 is fixed on the specific area 212. The data generator 230 can generate second gaze data when the gaze 292 is fixed on the specific area 212. The transmitter 240 can transmit the second gaze data to the apparatus 100, so that the apparatus 100 can receive information that the gaze is fixed on the specific area 212 based on the second gaze data.

Moreover, the apparatus 100 comprises a receiver 150 and a prompting system 160. The receiver 150 can receive the second gaze data after the terminal equipment 200 sends the second gaze data. The prompting system 160 can provide a prompt based on the second gaze data; for example, the prompting system 160 may render prompting information, play prompting sound, vibrate itself or do the like. Thus, the user 190 knows that the gaze is fixed on the specific area 212 of the terminal equipment 200.

In practice, one or more photos may be placed or displayed in the specific area 112 of the main body 110. For example, the users 190 and 290 are a couple of lovers. He 190 places the photo of his girlfriend 290 in the specific area 112. Whenever he 190 gazes at the photo, the apparatus 100 detects that his gaze 192 is fixed on the specific area 112 and transmits the gaze data to the terminal equipment 200 through a network, so that the terminal equipment 200 provides a prompt for her 290. Thus, whenever he 190 turns his gaze 192 to the photo, she 290 emotionally feels expression showing in his eyes.

Figure 2:
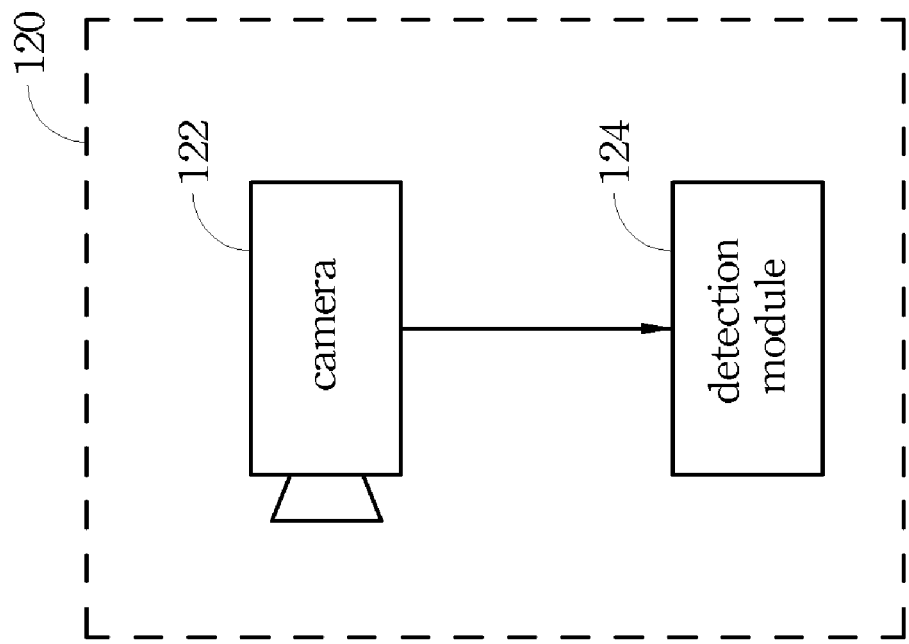
FIG. 2 is a block diagram illustrating the eye-movement detector of FIG. 1.
Figure 2:
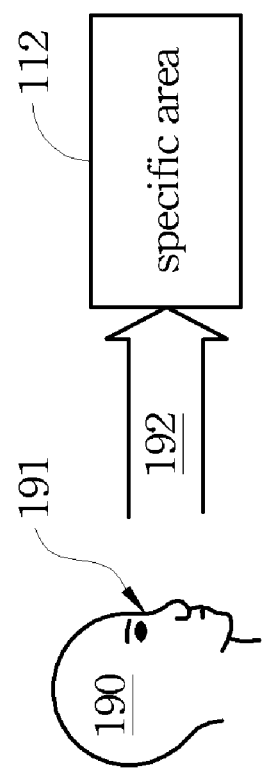

For a more complete understanding of the eye-movement detector 120, please refer to FIG. 2. FIG. 2 is a block diagram illustrating the eye-movement detector 120 of FIG. 1. In FIG. 2, the eye-movement detector 120 comprises a camera 122 and a detection module 124. The camera 122 can capture an captured image of at least one eye. The detection module 124 can check whether the gaze 192 is focused on the specific area 112 based on the captured image.

Furthermore, The camera 122 can capture the captured image of at least one eye 191 of the user 190. The detection module 124 can check whether the gaze 192 of the user 190 is fixed on the specific area 112 based on the captured image of the eyes 191. For example, the detection module 124 can find a position of the pupil of the eye 191 in the captured image and analyze where the gaze 192 of the user 190 is fixed based on the position of the pupil; alternatively, the detection module 124 can find a center of the iris of the eye 191 in the captured image and analyze where the gaze 192 of the user 190 is fixed based on the center of the iris.

Figure 3A:
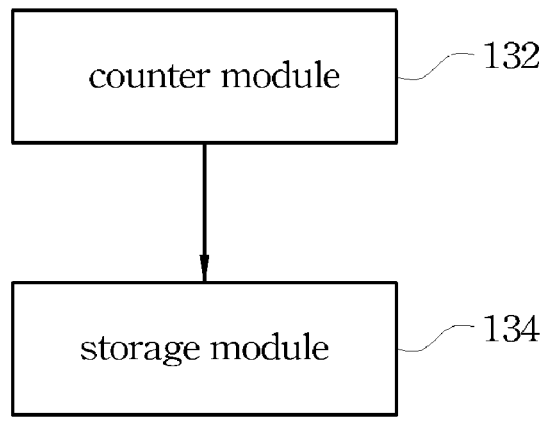
FIG. 3A is a block diagram illustrating the data generator of FIG. 1 according to one embodiment of the invention.
Figure 3B:
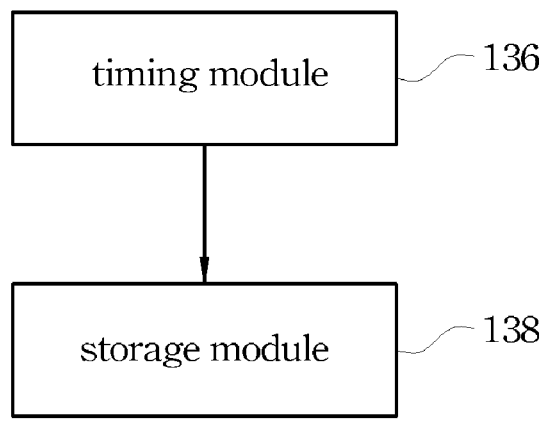
FIG. 3B is a block diagram illustrating the data generator of FIG. 1 according to another embodiment of the invention.

For a more complete understanding of the data generator 130, please refer to FIG. 3A and FIG. 3B. FIG. 3A is a block diagram illustrating the data generator 130 of FIG. 1 according to one embodiment of the invention; FIG. 3B is a block diagram illustrating the data generator 130 of FIG. 1 according to another embodiment of the invention.

In the FIG. 3A, the data generator 130 comprises a counter module 132 and a storage module 134. The counter module 132 can count the number of times the gaze is fixed on the specific area. The storage module 134 can record the number of times in the first gaze data. Therefore, the apparatus 100 transmits the first gaze data to the terminal equipment 200, where the first gaze data comprising the number of times acts as an index of expression of eye.

In the FIG. 3B, the data generator 130 comprises a timing module 136 and a storage module 138. The timing module 136 measures the time duration during which the gaze is fixed on the specific area. The storage module 138 can record the time duration in the first gaze data. Therefore, the apparatus 100 transmits the first gaze data to the terminal equipment 200, where the first gaze data comprising the time duration acts as an index of the expression of the eye.

Figure 4:
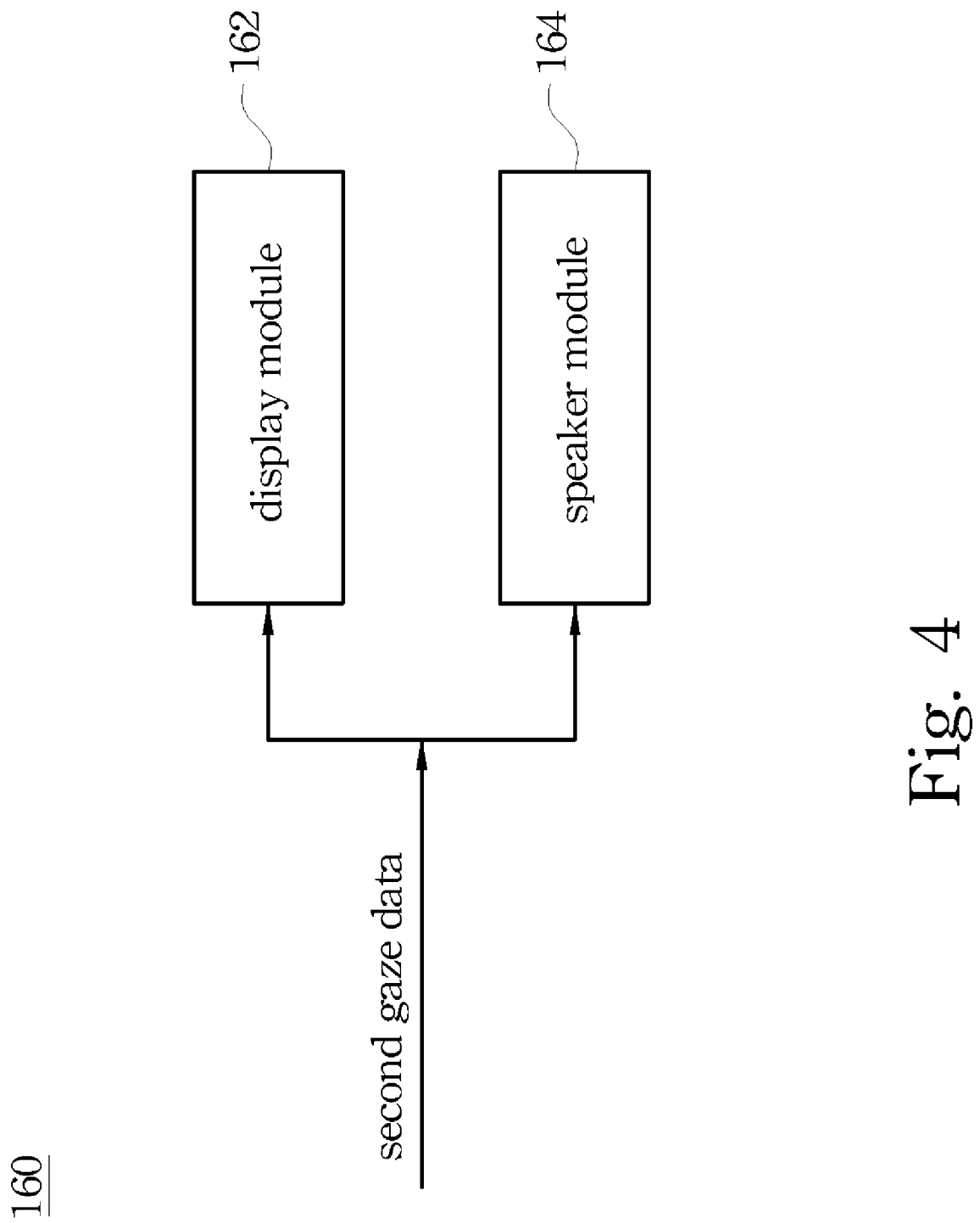
FIG. 4 is a block diagram illustrating the data prompting system of FIG. 1.

For a more complete understanding of the prompting system 160, please refer to FIG. 4. FIG. 4 is a block diagram illustrating the data prompting system 160 of FIG. 1. In FIG. 4, the prompting system 160 comprises a display module 162. The display module 162 can render the prompting information based on the second gaze data. For example, the display module 162 displays an icon and/or a text message as the prompting information based on the second gaze data received by the receiver 150, as shown in FIG. 1.

Additionally or alternatively, the prompting system 160 comprises a speaker module 164. The speaker module 164 can play the prompting sound based on the second gaze data. For example, the speaker module 164 plays the prompting sound with sound effects based on the second gaze data received by the receiver 150, as shown in FIG. 1.

Figure 5A:
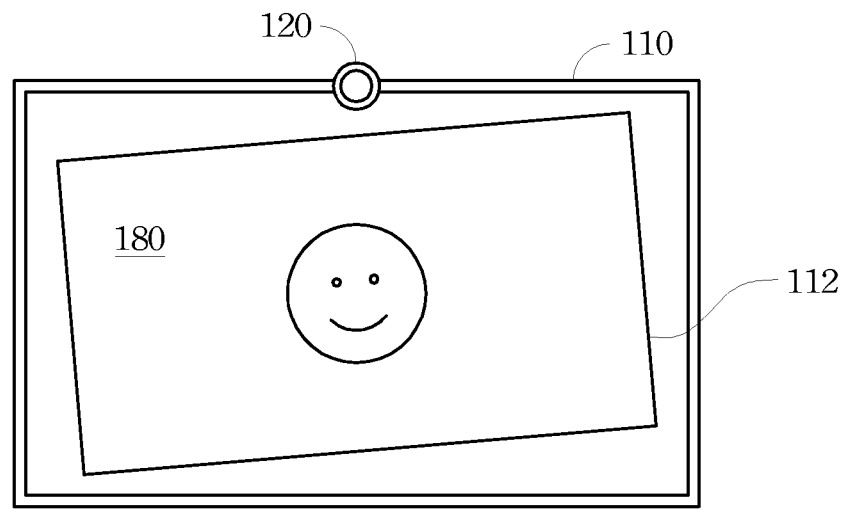
FIG. 5A is a schematic diagram illustrating the main body of FIG. 1 according to one embodiment of the invention.
Figure 5B:
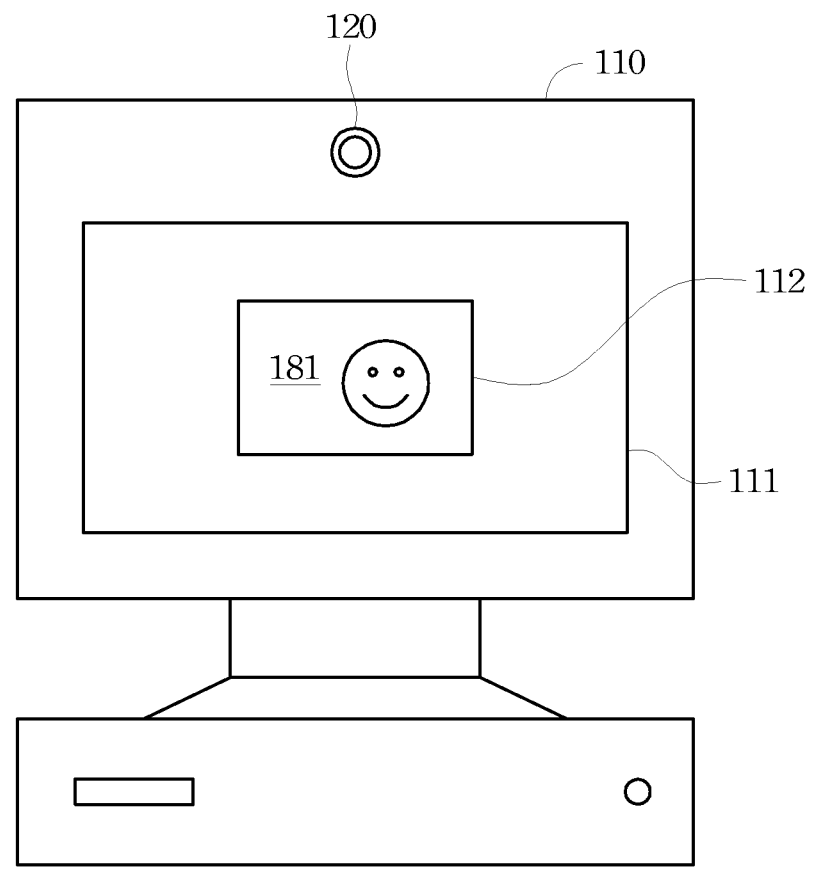
FIG. 5B is a schematic diagram illustrating the main body of FIG. 1 according to another embodiment of the invention.
Figure 5C:
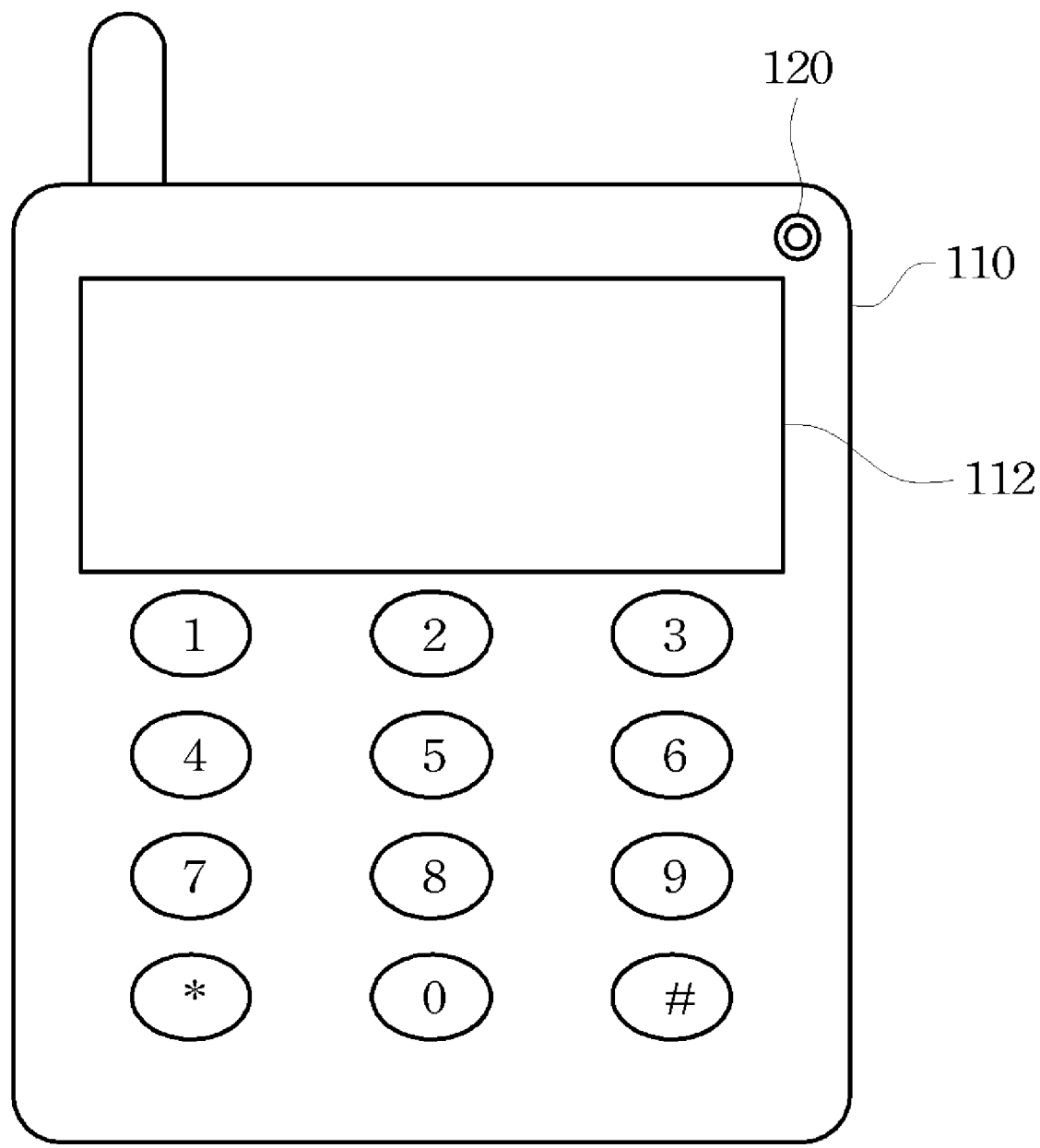
FIG. 5C is a schematic diagram illustrating the main body of FIG. 1 according to yet another embodiment of the invention.

For a more complete understanding of the main body 110, please refer to FIG. 5A, FIG. 5B and FIG. 5C. FIG. 5A is a schematic diagram illustrating the main body 110 of FIG. 1 according to one embodiment of the invention; FIG. 5B is a schematic diagram illustrating the main body 110 of FIG. 1 according to another embodiment of the invention; FIG. 5C is a schematic diagram illustrating the main body 110 of FIG. 1 according to yet another embodiment of the invention.

In the FIG. 5A, the main body 110 is a photo frame, such as a traditional photo frame or a digital photo frame, and its specific area 112 is capable of displaying a photo 180. The eye-movement detector 120 is inserted in the photo frame, so as to detect a gaze of a viewer and determine whether the gaze is fixed on the specific area 112. Moreover, the data generator 130, the transmitter 140, the receiver 150 and the prompting system 160, as shown in FIG. 1, may be disposed in the photo frame.

In the FIG. 5B, the main body 110 is a computer having a computer screen 111, and the computer screen 111 has the specific area 112 and shows an image 181 in the specific area 112. The eye-movement detector 120 may comprise a webcam inserted or configured in the computer, so as to detect a gaze of a viewer and determine whether the gaze is fixed on the specific area 112 of the computer screen 111. Moreover, the data generator 130, the transmitter 140, the receiver 150 and the prompting system 160, as shown in FIG. 1, may be software programs and/or hardware circuits integrated in the computer.

In the FIG. 5C, the main body 110 is a mobile phone, and the specific area 112 is a mobile phone screen of the mobile phone. The eye-movement detector 120 may comprise a camera inserted or configured in the mobile phone, so as to detect a gaze of a viewer and determine whether the gaze is fixed on the specific area 112. Moreover, the data generator 130, the transmitter 140, the receiver 150 and the prompting system 160, as shown in FIG. 1, may be software programs and/or hardware circuits integrated in the mobile phone.

Figure 6:
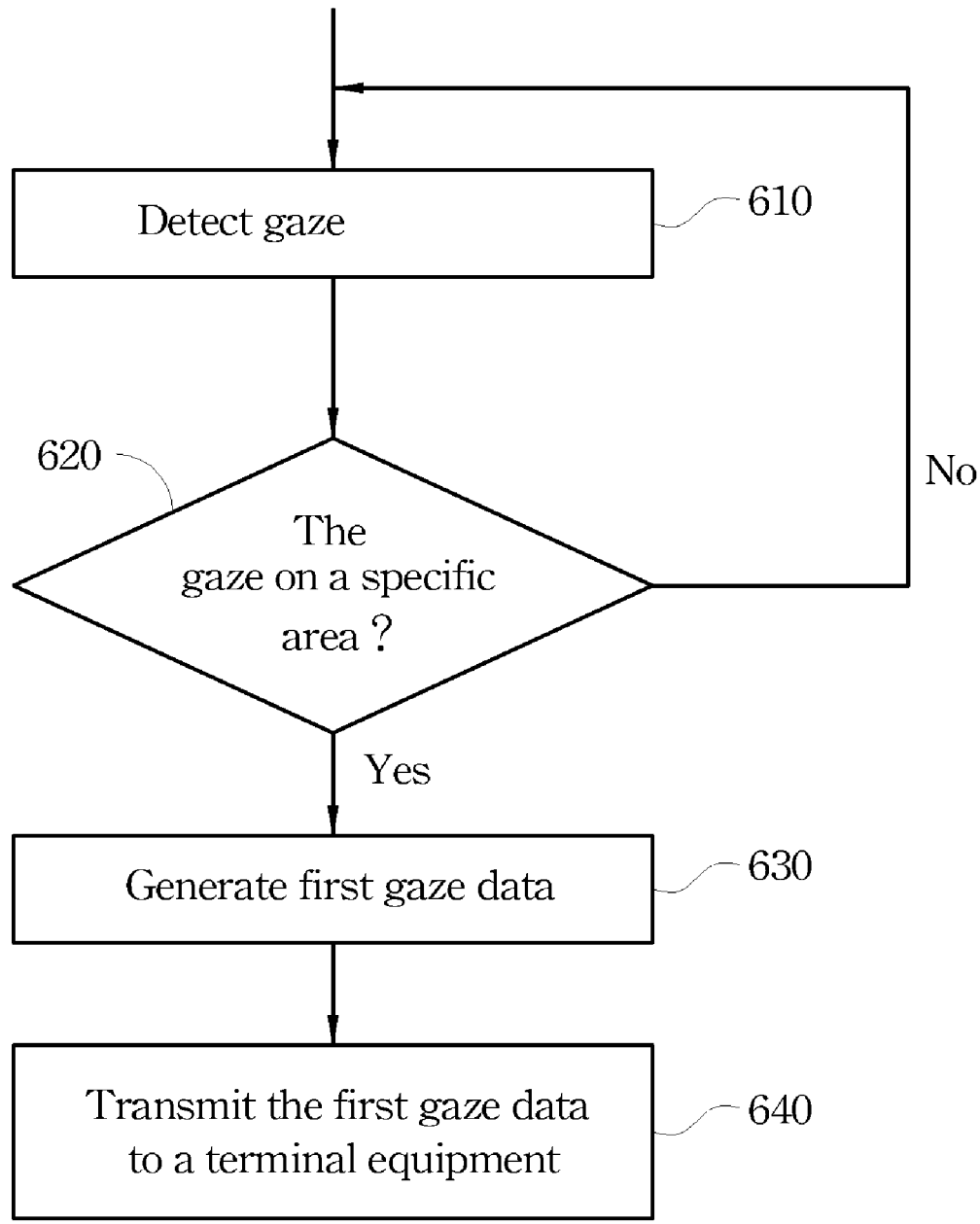
FIG. 6 is a method for recognizing a person's gaze according to one embodiment of the present invention.

Please refer to FIG. 6. FIG. 6 is a method 600 for recognizing a person's gaze according to one embodiment of the present invention. In FIG. 6, the method 600 comprises steps 610, 620, 630 and 640. In the method 600, it should be noted that one step might be performed in series, in parallel, in combination, or otherwise in conjunction with another if the specific order is not described or inferred in the embodiment. The apparatus of performing the method 600 is described in the preceding embodiment and, thus, are not repeated herein.

First, a first viewer's gaze is detected in step 610 and whether the gaze of the first viewer is fixed on a specific area is determined in step 620. Then, first gaze data are generated in step 630 if the gaze was fixed on the specific area as determined in step 620. Then, the first gaze data are transmitted to terminal equipment in step 640, so that the terminal equipment can receive the first gaze data and provide a prompt based on the first gaze data; for example, the terminal equipment may render prompting information, play prompting sound, vibrate itself or do the like. Moreover, if the gaze wasn't fixed on the specific area as determined in step 620, steps 610 and 620 are repeated in an iterative manner until the gaze is fixed on the specific area.

In the embodiment, the terminal equipment can detect a gaze of a second viewer and determining whether the gaze of the second viewer is fixed on another specific area. Then, the terminal equipment generates second gaze data when the gaze of the second viewer is fixed on said another specific area. Then, the terminal equipment sends the second gaze data, so that the method 600 is performed to receive the second gaze data for providing a prompt based on the second gaze data. For example, the method 600 may be performed to render prompting information based on the second gaze data; additionally or alternatively, the method 600 may be performed to play prompting sound.

During steps 610 and 620, a captured image of at least one eye is captured, so as to detect the gaze, and then whether the gaze is fixed on the specific area is checked based on the captured image. For example, a position of the pupil of the eye in the captured image is found, so as to analyze where the gaze is fixed based on the position of the pupil; alternatively, a center of the iris of the eye in the captured image is found, so as to analyze where the gaze is fixed based on the center of the iris.

Above step 630 may be performed to count the number of times the gaze is fixed on the specific area for recording the number of times in the first gaze data. Therefore, the first gaze data are transmitted to the terminal equipment in step 640, where the first gaze data comprising the number of times acts as an index of expression of eye.

Additionally or alternatively, above step 630 may be performed to measure time duration during which the gaze is fixed on the specific area for recording the time duration in the first gaze data. Therefore, the first gaze data are transmitted to the terminal equipment in step 640, where the first gaze data comprising the time duration acts as an index of expression of eye.

Any element in a claim that does not explicitly state "means for" performing a specified function, or "step for" performing a specific function, is not to be interpreted as a "means" or "step" clause as specified in 35 U.S.C. §112, sixth paragraph. In particular, the use of "step of" in the claims herein is not intended to invoke the provisions of 35 U.S.C. §112, sixth paragraph.

What is claimed is:

1. An apparatus for recognizing a person's gaze, comprising:
    a main body comprising a specific area;
    means for detecting whether a gaze is fixed on the specific area;
    means for generating first gaze data when the gaze is fixed on the specific area, wherein the generating means comprises: means for counting the number of times the gaze is fixed on the specific area; means for recording the number of times in the first gaze data; means for measuring time duration during which the gaze is fixed on the specific area; and means for recording the time duration in the first gaze data;
    means for transmitting the first gaze data to a terminal equipment, so that the terminal equipment provides prompt based on the first gaze data,
    means for receiving second gaze data after the terminal equipment sends the second gaze data; and
    means for providing the prompt based on the second gaze data.

2. The apparatus of claim 1, wherein the providing means comprises:
    means for rendering prompting information based on the second gaze data.

3. The apparatus of claim 1, wherein the providing means comprises:
    means for playing prompting sound based on the second gaze data.

4. The apparatus of claim 1, wherein the detecting means comprises:
    means for capturing a captured image of at least one eye; and
    means for checking whether the gaze is fixed on the specific area based on the captured image.

5. The apparatus of claim 1, wherein the main body is a photo frame and its specific area is capable of displaying a photo.

6. The apparatus of claim 1, wherein the main body is a computer having a computer screen, and the computer screen has the specific area and shows an image in the specific area.

7. The apparatus of claim 1, wherein the main body is a mobile phone, and the specific area is a mobile phone screen of the mobile phone.

8. A method for recognizing a person's gaze, comprising steps of:
    (a) detecting a gaze and determining whether the gaze is fixed on a specific area;
    (b) generating first gaze data when the gaze is fixed on the specific area, wherein the step (b) comprises: counting the number of times the gaze is fixed on the specific area; recording the number of times in the first gaze data; measuring time duration during which the gaze is fixed on the specific area; recording the time duration in the first gaze data;
    (c) transmitting the first gaze data to terminal equipment, so that the terminal equipment provides a prompt based on the first gaze data;
    (d) receiving second gaze data after the terminal equipment sends the second gaze data; and
    (e) providing the prompt based on the second gaze data.

9. The method of claim 8, wherein the step (e) comprises: rendering prompting information based on the second gaze data.

10. The method of claim 8, wherein the step (e) comprises: playing prompting sound based on the second gaze data.

11. The method of claim 8, wherein the step (a) comprises: capturing a captured image of at least one eye; and
    checking whether the gaze is fixed on the specific area based on the captured image.

* * * * *